United States Patent [19]

Robertson, II et al.

[11] Patent Number: 4,944,291

[45] Date of Patent: Jul. 31, 1990

[54] DEVICE AND PROCESS FOR HYGIENIC MOUTH TO MOUTH ARTIFICIAL RESPIRATION

[76] Inventors: G. Neil Robertson, II, 1801 Hanover Dr., B-904, Davis, Calif. 95616; Truman F. Allen, 316 California Ave., #326, Reno, Nev. 89509

[21] Appl. No.: 239,115

[22] Filed: Aug. 31, 1988

[51] Int. Cl.⁵ ............................................. A61M 16/00
[52] U.S. Cl. ............................ 128/203.11; 128/207.12
[58] Field of Search ....................... 128/202.28, 202.29, 128/203.11, 207.12

[56] References Cited

U.S. PATENT DOCUMENTS

| | | | |
|---|---|---|---|
| 3,017,880 | 1/1962 | Brook | 128/203.11 |
| 3,265,066 | 8/1966 | Katchis | 128/202.28 |
| 3,327,704 | 6/1967 | Bartlett, Jr. | 128/203.11 |
| 3,626,936 | 12/1971 | Barker | 128/203.11 |
| 4,535,765 | 8/1985 | Paoluccio et al. | 128/203.11 |

OTHER PUBLICATIONS

Intertech Brochure #138701 (4/87) 15M on Safe Response ™ Mouth-to-Mouth Mask, from Intertech Resources, Inc. #2275 Half Day Road, Suite 175, Bannockburn, Ill. 60015.

Primary Examiner—Edgar S. Burr
Assistant Examiner—Aaron J. Lewis
Attorney, Agent, or Firm—Jerry T. Kearns

[57] ABSTRACT

A device for use by an attendant performing hygienic mouth to mouth artificial respiration on a patient includes a mouth mask formed from a flexible elastomeric material configured for conforming sealing engagement over a patient's mouth. First and second tubes formed from a clear plastic material extend in sealing relation through the mouth mask. A check valve and mouthpiece are connected to the first tube for allowing an attendant to blow air into a patient's mouth, while preventing exhaled air from a patient from returning through the first tube to an attendant. An elbow and an attached flexible exhaust conduit are connected to the second tube for directing air exhaled from a patient away from an attendant. The flexible exhaust conduit may be pinched by an attendant to regulate the exhalation rate of a patient. An elongated flexible tether, formed integrally with the mouth mask, has a slotted portion through which a nose clip is inserted. The nose clip is formed from a hard elastomeric material for use in closing a patient's nose. The entire device is formed from inexpensive materials and is designed for disposal after one time use.

2 Claims, 3 Drawing Sheets

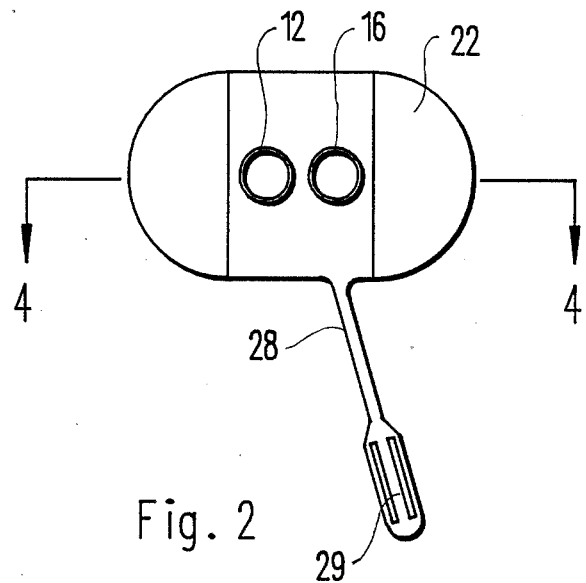
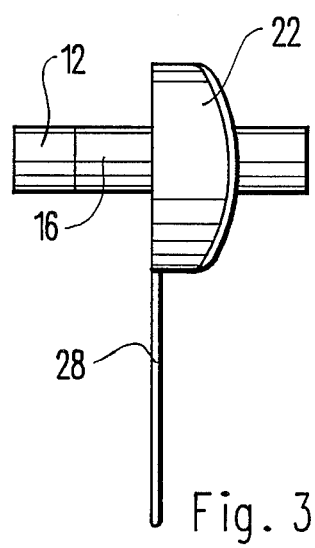
Fig. 2    Fig. 3
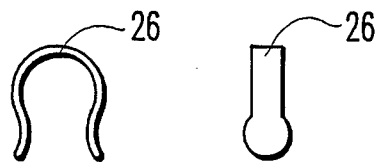
Fig. 5    Fig. 5A
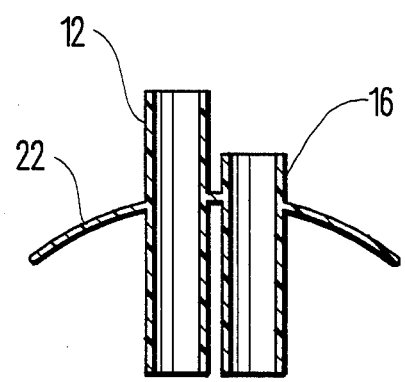
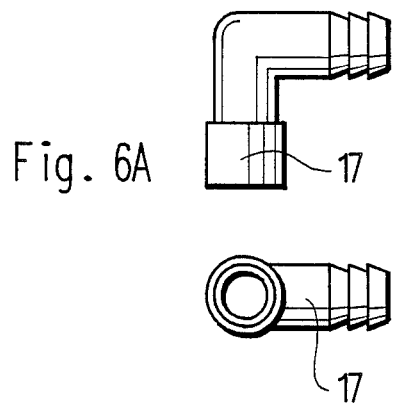
Fig. 4    Fig. 6A
Fig. 6

DEVICE AND PROCESS FOR HYGIENIC MOUTH TO MOUTH ARTIFICIAL RESPIRATION

RELATED APPLICATIONS

This application is related to Ser. No. 07/027,169, filed Mar. 17, 1987.

BACKGROUND OF THE INVENTION

1. Field of the Invention

The present invention relates to artificial respiration devices, and more particularly pertains to a device and process for administering mouth to mouth artificial respiration to a patient by an attendant. When a patient is not breathing, emergency treatment in the form of CPR commonly requires rapid administration of artificial respiration in order to restore respiratory function to the victim or patient.

2. Description of the Prior Art

Particularly with the increase of various contagious diseases, a number of devices have been developed in the prior art for facilitating the administering of mouth to mouth resuscitation while avoiding direct contact between the attendant administering the resuscitation and the patient or victim. These devices have generally included a tubular passage with a one-way check valve through which the attendant can force air into the patient's mouth (and lungs) while also providing means for allowing air to be exhaled by the patient in order to promote a normal respiratory cycle. For example, such a device is disclosed by A. S. Cross in U.S. Pat. No. 3,124,124, issued Mar. 10, 1964. Similar devices also adapted for facilitating mouth to mouth resuscitation are disclosed in a number of other U.S. Patents including for example, U.S. Pat. No. 3,957,046, issued May 18, 1976 to Harris; U.S. Pat. No. 4,535,765, issued Aug. 20, 1985, to Paoluccio et al; and U.S. Pat. No. 4,579,114, issued Apr. 1, 1986 to Gray et al. These additional patents are representative of further refinements in such devices. For example, the Paoluccio et al patent discloses such a device with separate conduits for forcing air into the patient's mouth and for allowing exhaled air to be exhausted to the atmosphere. It is of course obvious that additional prior art references have been directed towards similar devices for facilitating mouth to mouth resuscitation. However, it is believed that the above noted patents are representative of the design of such available devices.

Because of the importance of rapidly administering CPR to patient's or victims where respiration has stopped, further refinements have been found to be desirable in such devices in order to achieve objectives such as those set forth below in connection with the device of the present invention.

SUMMARY OF THE INVENTION

A device for use by an attendant performing hygienic mouth to mouth artificial respiration on a patient includes a mouth mask formed from a flexible elastomeric material configured for conforming sealing engagement over a patient's mouth. First and second tubes formed from a clear plastic material extend in sealing relation through the mouth mask. A check valve and mouthpiece are connected to the first tube for allowing an attendant to blow air into a patient's mouth, while preventing exhaled air from a patient from returning through the first tube to an attendant. An elbow and an attached flexible exhaust conduit are connected to the second tube for directing air exhaled from a patient away from an attendant. The flexible exhaust conduit may be pinched by an attendant to regulate the exhalation rate of a patient. An elongated flexible tether, formed integrally with the mouth mask, has a slotted portion through which a nose clip is inserted. The nose clip is formed from a hard elastomeric material for use in closing a patient's nose. The entire device is formed from inexpensive materials and is designed for disposal after one time use.

It is contemplated that the device will be marketed in zip-lock bag packaging in complete kits including: complete instructions as an aid in preventing panic, a pair of large sized medical examination gloves which prevent contact with a patient's body fluids, and a tongue depressor which enables evacuation of the patient's oral cavity other than digitally.

The method of using the device of the present invention comprises the following steps:

(1) The attendant opens the zip-lock kit bag, puts on the latex examination gloves and then utilizes the tongue depressor to flatten the patient's tongue and clear the oral cavity.

(2) The device is inserted into the patient's mouth, with the mouth mask in air tight sealing engagement over the patient's mouth. The device, once inserted, keeps the patient's tongue flat, reducing the risk of the victim's tongue falling back down the throat and being swallowed.

(3) The nose clip is placed over the patient's nose.

(4) The attendant administers artificial respiration by blowing through the mouthpiece and check valve of the first tube.

(5) The patient's exhaled air is exhausted remotely from the attendant through the exhaust conduit. The attendant may regulate the patient's exhalation rate by pinching the flexible exhaust conduit.

(6) Upon cessation of CPR, the device is removed from the patient's mouth, and deposited back into its original ziplock plastic bag container, along with the tongue depressor and the latex examination gloves. The zip-lock bag is then closed and the entire unit is discarded.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved device and process for hygienic mouth to mouth artificial respiration which has all the advantages of the prior art artificial respiration devices and none of the disadvantages.

It is another object of the present invention to provide a new and improved device and process for hygienic mouth to mouth artificial respiration which may be easily and efficiently manufactured and marketed.

It is a further object of the present invention to provide a new and improved device and process for hygienic mouth to mouth artificial respiration which is of a durable and reliable construction.

An even further object of the present invention is to provide a new and improved device and process for hygienic mouth to mouth artificial respiration which is susceptible of a low cost of manufacture with regard to both materials and labor, and which accordingly is then susceptible of low prices of sale to the consuming public, thereby making such artificial respiration devices economically available to the buying public.

Still another object of the present invention is to provide a new and improved device for administering mouth to mouth artificial respiration to a patient by an attendant.

Even still another object of the present invention is to provide a device for administering hygienic artificial respiration having a simplified construction such that its appearance makes its usage readily apparent and obvious.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which a preferred embodiment of the invention is illustrated.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is an end view of the device of the present invention.

FIG. 3 is a side view of the device of the present invention.

FIG. 4 is a cross sectional view, taken along line 4—4 of FIG. 2.

FIG. 5 is an end view of the nose clip.
FIG. 5A is a side view of the nose clip.
FIG. 6 is an end view of the exhaust tube elbow.
FIG. 6A is a side view of the exhaust tube elbow.

DESCRIPTION OF THE PREFERRED EMBODIMENT

Figure 1:
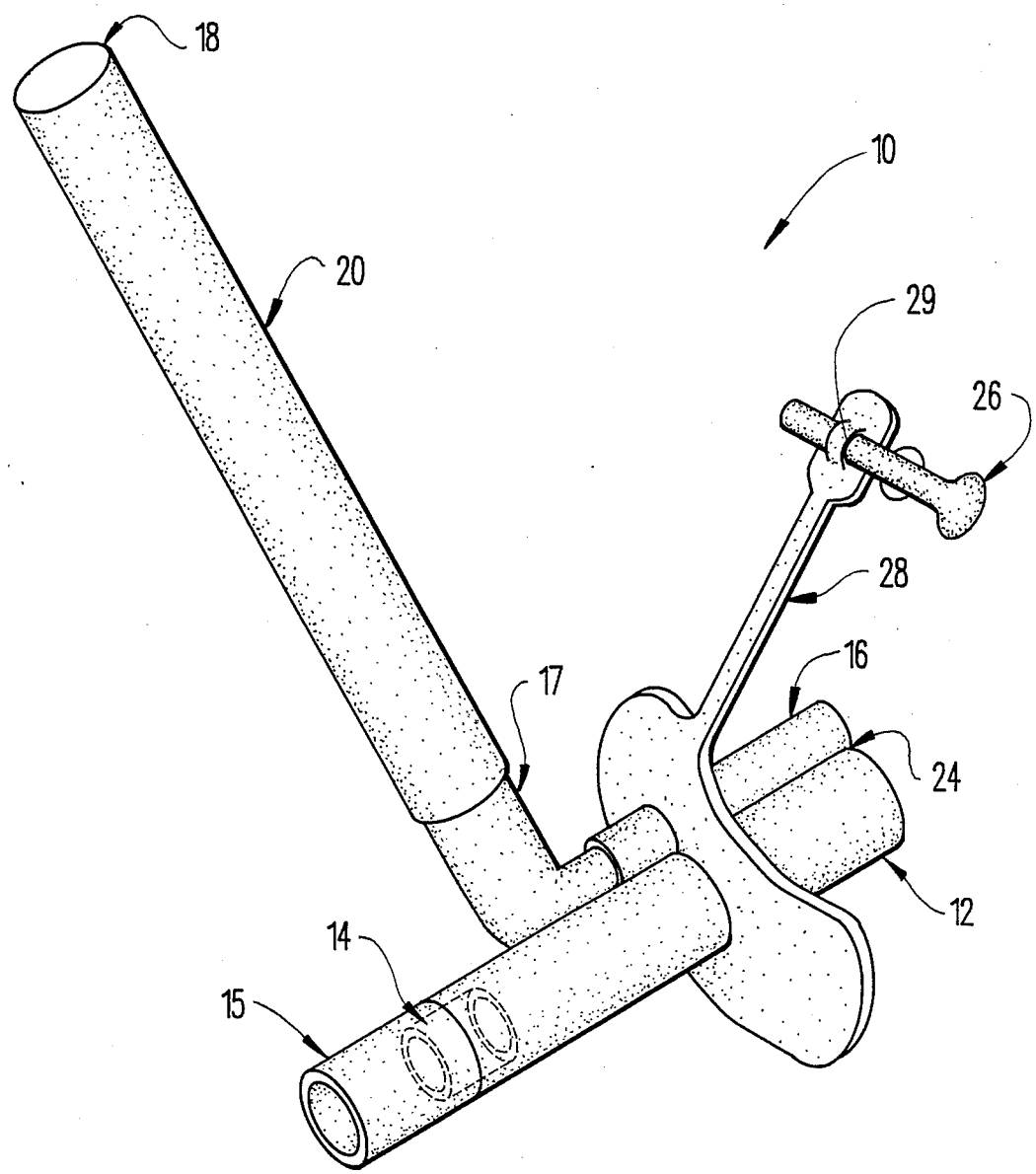
FIG. 1 is a pictorial view of the apparatus of the present invention.

With reference now to the drawings, and in particular to FIG. 1 thereof, a new and improved device and process for hygienic mouth to mouth artificial respiration embodying the principles and concepts of the present invention and generally designated by the reference numeral 10 will be described.

More specifically, it will be noted that the device 10 of the invention includes a first short tube 12 including a conventional check valve 14 as disclosed in U.S. Pat. No. 3,124,124, and a mouth piece 15. For ease of use, the mouth piece 15 is a pliable plastic extension mouthpiece, properly sized to facilitate blowing directly into the valve by the rescuer.

The check valve 14 is of conventional construction as noted above, and is arranged in the first short tube 12 for only allowing air flow from the attendant toward the patient. Thus, with the apparatus eliminating the need for direct contact between the patient and attendant, the one way check valve 14 further assures that the attendant will not inhale air from the patient's mouth or lungs. Unlike many other valves on prior art CPR devices which direct the airflow (input or exhaust) within the valve itself, the device of the present invention utilizes a true one-way valve that is described as a "positive action" valve. As such, it does not direct air flow within the valve, but can only process air in one direction. Contrary to the prior art valves of the type which rely upon exhaust air to close the valve and reverse the flow of air, the valve utilized in the inventive device snaps shut immediately when supply air ceases. This feature also diminishes the potential for allowing exhaust vapor or fluids to escape, however minutely, around the valve diaphragm before it seals tightly, potentially contaminating the rescuer. This valve is patented under U.S. Pat. No. 3,124,124, the entire disclosure of which is hereby incorporated by reference herein.

The apparatus further includes a second mouth inserted tube 16 connected via an elbow 17 with a conduit 20 having an outlet 18 at one end. The exhaust conduit 20 is preferably formed from a flexible material, which can be pinched or manipulated by the attendant to selectively block air flow through the second tube 16 and thereby regulate exhalation by the patient. Unlike prior art CPR devices which allow moisture-laden exhaust air to escape near the rescuer's nose or mouth, the device of the present invention exhausts the patient's exhaled air remote from the immediate vicinity of the rescuer's breathing, thereby reducing risk of contamination due to inhaling moisture-laden exhaust air. The exhaust conduit 20 is circular and free of obstruction, facilitating air movement. Also, it is made of a sufficiently pliable clear plastic material so as to be easily pinched together, preventing exhalation until sufficient air is blown into the victim's lungs, at which time it is released allowing the air to exhaust and the victim's lungs to empty. The clear plastic material allows any obstructions in the tube to be easily detected by visual inspection.

In the event of reverse peristalsis, unlike many prior art CPR devices with air flow activated closing valves, as describe supra, which direct the air flow within the valve and which therefore can become fouled and useless, the check valve 14 utilized in the device of the present invention can be cleared by removing the device and blowing through the valve to clear it. Also, should the tube 16 or the exhaust conduit 20 become fouled, they can be cleared by removing the device from the victim's mouth, shaking it vigorously to remove any fouling, whereupon it can be reinserted and resuscitation efforts resumed.

A mouth mask 22 is arranged for positioning a common end 24 of both the first 12 and second 16 tubes within the patient's mouth.

The device 10, as described above, particularly facilitates administering of mouth-to-mouth artificial respiration to a patient by an attendant. In particular, the short first tube 12 enhances the ability of the attendant to forcefully direct air into the patient's lungs. A longer tube would be undesirable because of the compressible nature of air within the tube which would tend to interfere with the amount of air delivered to the patient's mouth and lungs by the attendant.

At the same time, the longer second tube 16 and attached exhaust conduit 20 assures that the exhaust 18 is remote from the attendant, so that air exhaled by the patient or victim passes into the surrounding environment without being directly inhaled by the attendant.

A nose clip 26 is secured, by insertion through a slotted portion 29 of a tether 28, to the mouth mask 22. Thus, the nose clip 26 can be employed by the attendant for closing the patient's nose to further facilitate operation of the apparatus through the patient's mouth. As in conventional manual CPR, where the nose is occluded, the nose clip insures that no CPR is conducted through the nasal passages, thereby preventing nasal congestion from fouling the bronchia. At the same time, the nose clip is preferably formed from a relatively hard elastomeric material to assure its proper functioning.

The mouth mask 22 is formed in common with the tubes 12 and 16, thus providing a sealed air-tight component. The common end 24 of the first 12 and second 16 tubes extends through and substantially beyond the mouth mask 22, in order to enter into the mouth of the patient when the mouth mask is in overlying engagement with the patient's mouth. The mouth mask 22 surrounds the inlet 12 and exhaust 16 tubes at a distance above the mouth insertion ends 24 and is made of a pliable clear plastic material which readily adapts to the shape of the victim's mouth, thereby providing an air tight seal.

The first 12 and second 16 tubes, as well as the mouth mask 22, are preferably formed from relatively soft elastomeric material, preferably polyvinylchloride, to facilitate manipulation of the device 10 by the attendant. The nose clip is preferably formed from a relatively hard elastomeric material, also polyvinylchloride, in order to perform its intended function. The flexible nature of the device 10 allows storage in a compact sealed container, which maintains hygienic conditions for the device prior to use.

The above described construction of the device 10 is susceptible of economical mass production, thus allowing the device 10 to be sufficiently inexpensive for facilitating its disposal after one time use to further assure hygienic conditions.

Figure 7:
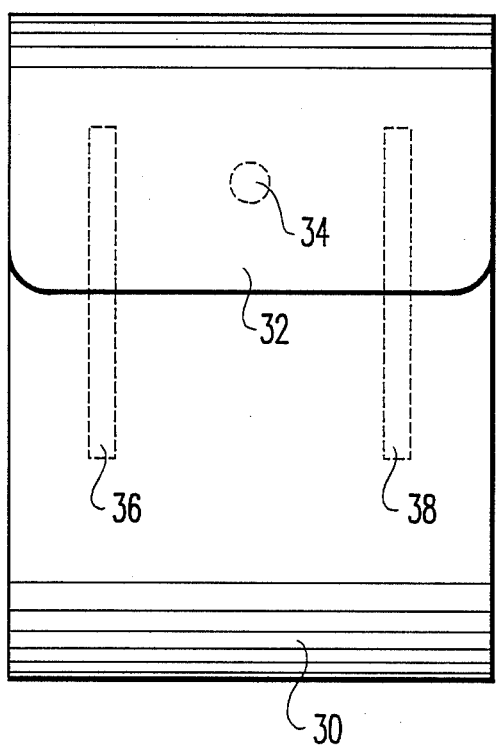
FIG. 7 is a front view of a storage and carrying pouch for the device of the present invention.
Figure 8:
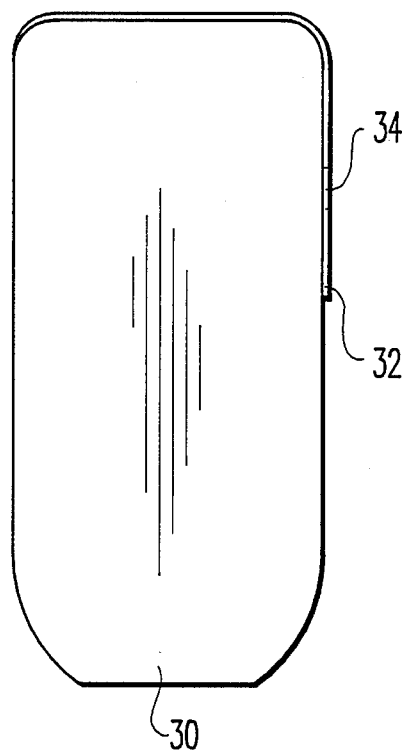
FIG. 8 is a side view of the storage pouch.
Figure 9:
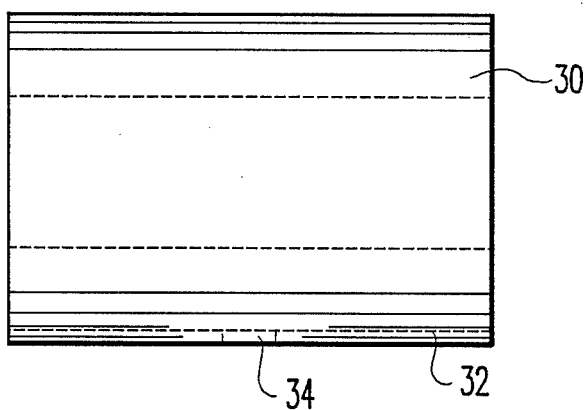
FIG. 9 is an end view of the storage pouch.

It is contemplated that the device 10 will be sold in complete kits packaged in zip-lock plastic bags including CPR instruction, a tongue depressor and latex examination gloves. As shown in FIGS. 7-9, the kit may be stored and transported for convenient availability in a pouch 30 having a closure flap 32 secured by a snap fastener 34. A pair of slots 36 and 38 are provided for securing the pouch on an individual's belt.

The method of utilizing the device of the present invention includes the steps of: opening the zip-lock bag; putting on the latex examination gloves; flattening the patient's tongue and clearing the patient's oral cavity utilizing the tongue depressor; inserting the first ends of the first and second tubes into the patient's mouth, with the mouth mask in air tight sealing engagement over the patient's mouth; placing the nose clip over the patient's nose; administering artificial respiration by blowing through the mouthpiece and check valve of the first tube; exhausting the patient's exhaled air remotely from the attendant through the exhaust conduit; regulating the patient's exhalation rate by pinching the flexible exhaust conduit; removing the device from the patient's mouth; depositing the device, the tongue depressor and the latex examination gloves back into the zip lock bag; and discarding the zip lock bag and contents.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the U.S. is as follows:

1. A device for use by an attendant in performing hygienic mouth to mouth artificial respiration on a patient, comprising:

a mouth mask formed from a flexible elastomeric material configured for conforming and sealing engagement over a patient's mouth;

a first tube formed from a clear plastic flexible material extending in sealing relation through said mask;

a first end of said first tube extending substantially through said mask and adapted for insertion into a patient's mouth;

a second end of said first tube extending substantially through said mask and having a mouthpiece adapted for insertion into an attendant's mouth;

a one way check valve in said first tube for allowing air to be blown into said second end by an attendant and out said first end into a patient's mouth and for preventing exhaled air from a patient from returning through said second end;

a second tube formed from a clear plastic flexible material extending in sealing relation through said mask, adjacent said first tube;

a first end of said second tube extending substantially through said mask and adapted for insertion into a patient's mouth;

a second end of said second tube extending substantially through said mask and having an elbow for directing exhaled air from a patient away from an attendant;

an elongated exhaust air conduit formed from a clear flexible plastic material connected to said elbow, said conduit having an outlet disposed remotely from said mouthpiece on said first tube;

an elongated flexible tether formed from an elastomeric material integrally with said mask;

a slotted portion formed adjacent a free end of said tether;

a nose clip inserted through said slotted portion and adapted for sealing engagement with a patient's nose; and said tether extending from a top portion of said mask and dimensioned to position said nose clip adjacent a patient's nose upon placement of said mask into engagement with a patient's mouth.

2. A process for use by an attendant in administering hygienic mouth to mouth artificial respiration to a patient, comprising the steps of:

(1) providing:

a mouth mask formed from a flexible elastomeric material configured for conforming and sealing engagement over a patient's mouth;

a first tube formed from a clear plastic material extending in sealing relation through said mask;

a first end of said first tube extending substantially through said mask and adapted for insertion into a patient's mouth;

a second end of said first tube extending substantially through said mask and having a mouthpiece adapted for insertion into an attendant's mouth;

a one way check valve in said first tube for allowing air to be blown into said second end by an attendant and out said first end into a patient's mouth and for preventing exhaled air from a patient from returning through said second end;

a second tube formed from a clear plastic material extending in sealing relation through said mask, adjacent said first tube;

a first end of said second tube extending substantially through said mask and adapted for insertion into a patient's mouth;

a second end of said second tube extending substantially through said mask and having an elbow for directing exhaled air from a patient away from an attendant;

an elongated exhaust air conduit formed from a clear flexible plastic material connected to said elbow, said conduit having an outlet disposed remotely from said mouthpiece on said first tube;

an elongated flexible tether formed from an elastomeric material integrally with said mask;

a slotted portion formed adjacent a free end of said tether;

a nose clip inserted through said slotted portion and adapted for sealing engagement with a patient's nose; and said tether extending from a top portion of said mask and dimensioned to position said nose clip adjacent a patient's nose upon placement of said mask into engagement with a patient's mouth.

a zip-lock plastic bag for storing and transporting said device;

a tongue depressor;

a pair of latex examination gloves;

(2) opening the zip-lock bag;

(3) putting on the latex examination gloves;

(4) flattening the patient's tongue and clearing the pateint's oral cavity utilizing the tongue depressor;

(5) inserting said first ends of said first and second tubes into the patient's mouth, with the mouth mask in air tight sealing engagement over the patient's mouth;

(6) placing said nose clip over the patient's nose;

(7) administering artificial respiration by blowing through said mouthpiece and check valve of said first tube;

(8) exhausting the patient's exhaled air remotely from the attendant through said exhaust conduit;

(9) regulating the patient's exhalation rate as required by pinching said flexible exhaust conduit;

(10) removing the device from the patient's mouth;

(11) depositing said device, said tongue depressor and said latex examination gloves back into said zip lock bag; and

(12) discarding said zip lock bag and contents.

* * * * *